(12) United States Patent
Arun et al.

(10) Patent No.: US 10,485,665 B2
(45) Date of Patent: Nov. 26, 2019

(54) APPARATUS AND METHOD FOR CONSTRUCTING IMPLANTABLE CARTILAGE STRUCTURES

(71) Applicant: ReconstratA, LLC, Baltimore, MD (US)

(72) Inventors: Anirudh Arun, Baltimore, MD (US); Angelo Alberto Leto Barone, Baltimore, MD (US)

(73) Assignee: ReconstratA, LLC, Baltimore, MD (US)

( * ) Notice: Subject to any disclaimer, the term of this patent is extended or adjusted under 35 U.S.C. 154(b) by 147 days.

(21) Appl. No.: 15/372,619

(22) Filed: Dec. 8, 2016

(65) Prior Publication Data

US 2017/0165078 A1   Jun. 15, 2017

Related U.S. Application Data

(60) Provisional application No. 62/265,085, filed on Dec. 9, 2015.

(51) Int. Cl.
*A61F 2/30* (2006.01)
*A61L 27/36* (2006.01)
*A61F 2/18* (2006.01)

(52) U.S. Cl.
CPC ............ *A61F 2/30942* (2013.01); *A61F 2/18* (2013.01); *A61L 27/3612* (2013.01);
(Continued)

(58) Field of Classification Search
CPC ........ A61F 2002/3096; A61F 2240/004; A61F 2/30942
See application file for complete search history.

(56) References Cited

U.S. PATENT DOCUMENTS 5,326,370 A   7/1994 Love et al.
5,326,371 A   7/1994 Love et al.
(Continued)

FOREIGN PATENT DOCUMENTS

EP   2528543 A   2/2012

OTHER PUBLICATIONS

Transmittal; International Search Report; and Written Opinion of the International Searching Authority for International Application No. PCT/US2016/065762 dated Apr. 4, 2017.

*Primary Examiner* — Mark A Osele
*Assistant Examiner* — Christopher C Caillouet
(74) *Attorney, Agent, or Firm* — Katten Muchin Rosenman LLP

(57) ABSTRACT

Apparatus and method for constructing a cartilage structure preferably has a first plate, and a blade mounted over the first plate. The blade preferably has (i) a predetermined shape, and (ii) a cutting edge protruding from the first plate and configured to cut a cartilage into the predetermined shape. A second plate preferably has a guide imprint adjacent a surface thereof, the guide imprint having a shape complimentary to the predetermined shape of the blade. A press preferably has (i) a first surface configured to mount the first plate, and (ii) a second surface configured to mount the second plate. Actuation structure is preferably configured to press together the press first and second surfaces to thereby cause the blade to cut the cartilage in the predetermined shape. The method utilizes similar structure to prepare at least two cartilages, which are joined together to form a three-dimensional cartilage structure.

14 Claims, 13 Drawing Sheets

(52) U.S. Cl.
CPC ....... *A61L 27/3654* (2013.01); *A61F 2/30756* (2013.01); *A61F 2002/183* (2013.01); *A61F 2002/3096* (2013.01); *A61F 2240/001* (2013.01); *A61F 2240/002* (2013.01); *A61F 2240/004* (2013.01); *A61L 2430/06* (2013.01)

(56) References Cited

U.S. PATENT DOCUMENTS

| | | |
|---|---|---|
| 5,425,741 A | 6/1995 | Lemp et al. |
| 5,571,174 A | 11/1996 | Love et al. |
| 5,609,600 A | 3/1997 | Love et al. |
| 5,653,749 A | 8/1997 | Love et al. |
| 5,662,705 A | 9/1997 | Love et al. |
| 5,788,625 A | 8/1998 | Plouhar et al. |
| 6,027,773 A | 2/2000 | Sterr et al. |
| 6,491,511 B1 | 12/2002 | Duran et al. |
| 6,679,914 B1 * | 1/2004 | Gabbay .................. A61F 2/3872 623/11.11 |
| 7,156,814 B1 | 1/2007 | Williamson et al. |
| 7,229,820 B2 | 6/2007 | Wilson |
| 7,618,653 B2 | 11/2009 | Xu |
| 3,028,837 A1 | 10/2011 | Gerstle et al. |
| 8,486,074 B2 | 7/2013 | Steiner et al. |
| 8,535,315 B2 | 9/2013 | Wong et al. |
| 8,568,480 B2 | 10/2013 | Fitz et al. |
| 9,149,295 B1 | 10/2015 | Condon |
| 2007/0270948 A1 | 11/2007 | Wuh |
| 2008/0039954 A1 | 2/2008 | Long et al. |
| 2009/0018465 A1 | 1/2009 | Hessel et al. |
| 2010/0075896 A9 | 3/2010 | Vucicevic et al. |
| 2010/0286693 A1 | 11/2010 | Steinhardt et al. |
| 2011/0264236 A1 | 10/2011 | Bassett et al. |
| 2012/0189669 A1 | 7/2012 | Altschuler |
| 2012/0191093 A1 | 7/2012 | Wong et al. |
| 2014/0228953 A1 | 8/2014 | Kang et al. |

\* cited by examiner

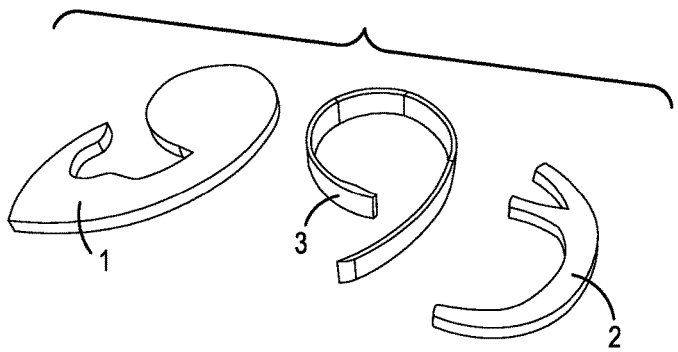
FIG. 1A
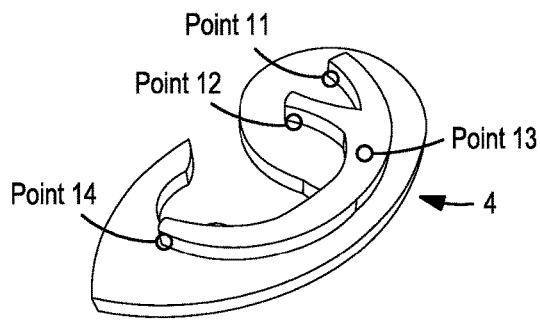
FIG. 1B
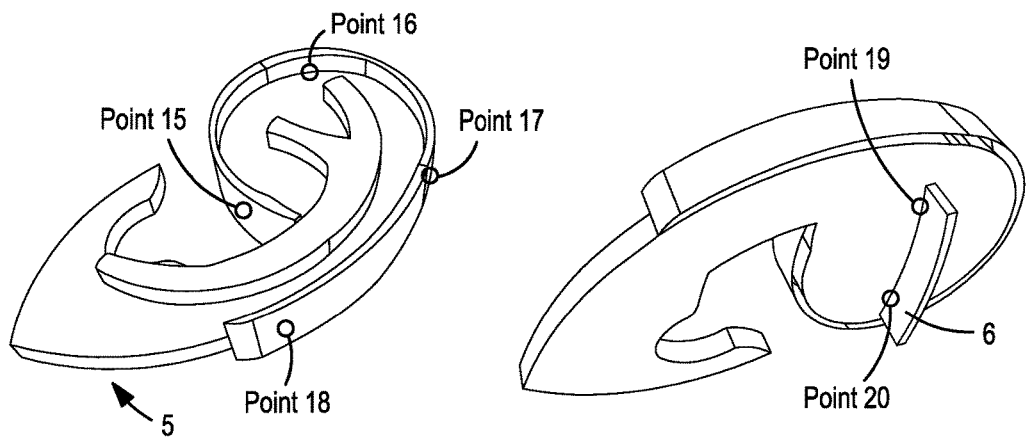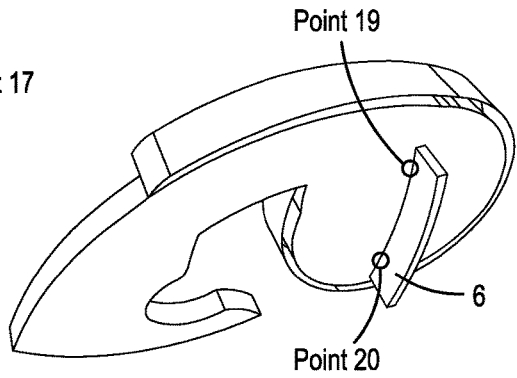
FIG. 1C     FIG. 1D

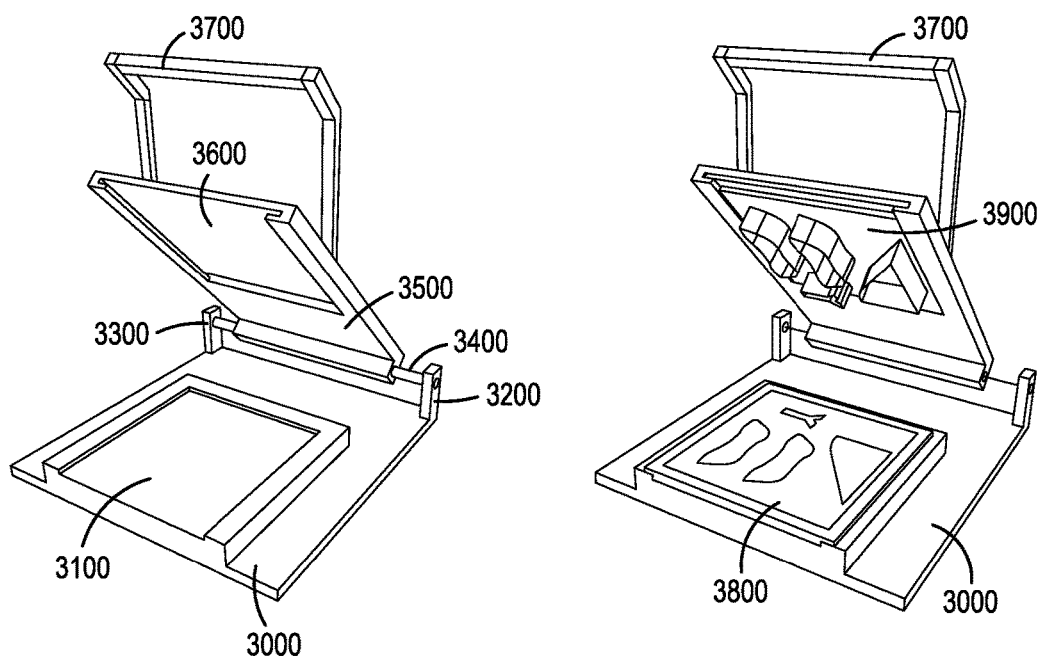
FIG. 6A  FIG. 6B

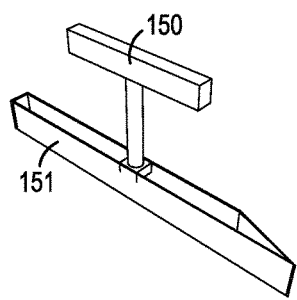
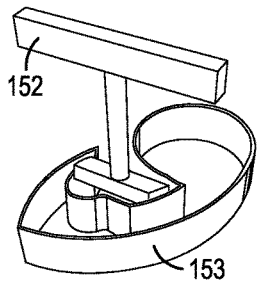
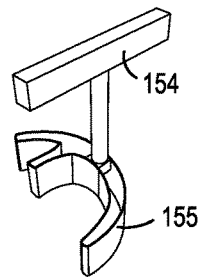
FIG. 7A   FIG. 7B   FIG. 7C
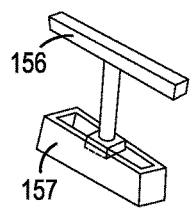
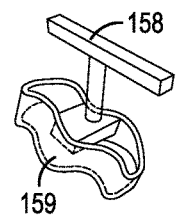
FIG. 7D   FIG. 7E
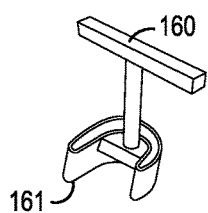
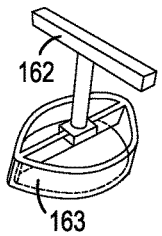
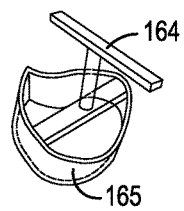
FIG. 7F   FIG. 7G   FIG. 7H

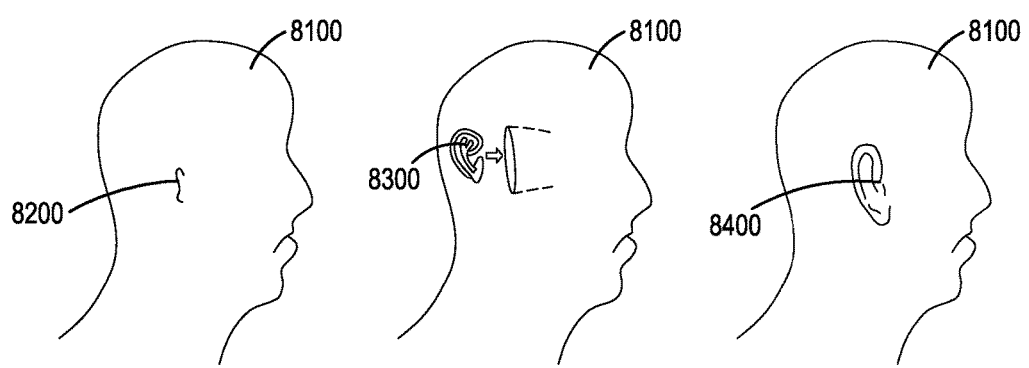
FIG. 8A　　FIG. 8B　　FIG. 8C

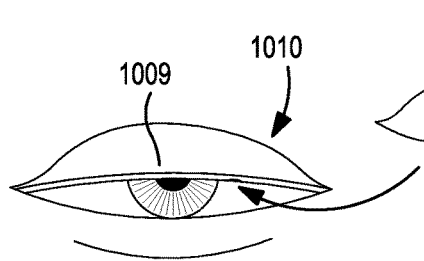 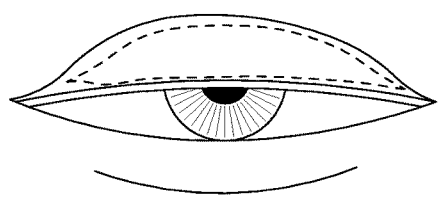
FIG. 10A  FIG. 10B  FIG. 10C

APPARATUS AND METHOD FOR CONSTRUCTING IMPLANTABLE CARTILAGE STRUCTURES

The subject application claims priority to U.S. provisional Patent Appln. No. 62/265,085, filed Dec. 9, 2015, the entire contents of which are incorporated herein by reference.

FIELD OF THE INVENTION

The present invention relates to the molding of cartilage derived from (i) the patient and/or a cadaveric source, and/or (ii) other dense implantable materials, into precise shapes, which, when subsequently assembled, can form a model of the human ear and/or nose and/or eyelid and/or other animal structure to be used for subsequent reconstruction, for example, in the field of plastic surgery.

BACKGROUND OF THE INVENTION

The external ear, also known as the auricle, is an important bilateral organ that allows convergence of sound waves to the middle and inner ear, allowing for the detection of sounds by the brain. Furthermore, auricles provide an important function in supporting glasses in patients who require vision correction. Additionally, auricles represent important aesthetic subunits of the human face due to their central position and clear visibility. Any alteration of its shape either from birth or acquired (after a trauma) represents a significant psychological burden for patients worldwide.

Microtia is a common malformation that presents with an abnormally shaped absent ear at birth. It has been calculated that microtia occurs at a rate of 0.83 to 17.4 per 10,000 live births in the general population. This range varies among regions, and is higher in Hispanics, Asians, Native Americans, and Andeans. Although this number may seem small, the number of cases present in the general population at any time is high and correction of ear deformity is in demand in these young patients.

Currently, the so-called Nagata technique represents the gold standard for surgical treatment of such deformities. In this long and technically challenging surgical technique, a large fraction of rib cartilage from the patient is harvested, and the surgeon, typically a plastic and reconstructive surgeon, carefully carves the rib cartilage to create several pieces that combined in a complex construct create a mold of the ear similar to that of the normal ear. This cartilage is then implanted under the skin where the ear is missing. Alternatively, a cadaver donor is used and the rib cartilage is available for immediate molding by the surgeon. Either way, this technique helps to restore ear form and function. The presence of a plastic surgeon who has obtained specific and additional training to perform such procedures is mandatory for a successful ear reconstruction with this technique. Surgeon-to-surgeon variability in skill sets in cartilage carving techniques render results suboptimal in some cases.

In addition to malformations like microtia, which are present since birth, acquired ear deformities are extremely common, accounting for a high percentage of all facial plastic surgery consults requested by Emergency Departments worldwide. These include trauma, such as dog bites or combat wounds, or resection to eradicate cancers, such as melanoma and non-melanoma skin cancers. Despite the finest reconstructive efforts, replantation of these ears are often not successful, leaving the patient malformed and without an auricle. These deformities, either congenital (from birth) or acquired (for trauma) can involve other cartilages in the body, including the nose cartilage. The nose is made of several pieces of cartilage that combined together create the septum, the lateral walls and the tip. For this reason, rhinoplasty, either for reconstructive purposes after trauma or for cosmetic purposes is one of the most complex and sought after procedures in Plastic Surgery. Eyelid (tarsus) reconstruction is another common reconstructive procedure for cosmetic and medical purposes, requiring a thin disc of cartilage to provide the framework for the final structure.

Existing patents do not appear to describe a process of developing a model of the human ear, nose, or eyelid cartilage from existing body tissues using a mechanical device. No patents exist that describe the development of implantable models of human ear, nose, or eyelid cartilage from either autologous cartilage or synthetic materials.

Patents related to the background of the invention include U.S. Pat. Nos. 6,491,511B1, 5,571,174A, 5,662,705A, and 5,326,371A, which detail the development of heart valves from pericardial tissue using shape specific dies. However, the quality of tissue is vastly different from the dense material required for cartilaginous structures. Additionally, they describe no overall processing of individual components into more complex structures, which is a notable feature according to the present invention, allowing for intricate 3-dimensional shapes to be generated from the original substrate. Other patent publications, such as US20140228953A1, US20110264236A1, and US20090018465A1 describe a preformed and implantable model of the ear. Aesthetic success of such implants can be limited, as the body's immune system typically reacts against foreign materials. As a result, the best results will be achieved by reshaping tissue generated from the patient's own cartilage, a process not addressed by existing patents.

In addition, U.S. Pat. No. 9,149,295 describes a system that harvests cartilage, trims and cuts it using a punch system, with a variety of cutters, to create precise configurations for tympanoplasty reconstructions. The present invention, however, has cutters shaped for ears, noses, and eyelids (not tympanic membrane), and the present invention mechanisms of action are larger presses, which the '295 patent system does not utilize. U.S. Pat. No. 8,535,315 describes a guillotine-like device to cut thin slices of costal cartilage of user-defined thickness. Vertical cutting of the cartilage is less advantageous and less accurate than the horizontally oriented blade according to the present invention. The thickness in the '315 patent is determined by blade separation, versus the present invention, which uses a vertically adjustable platform to position the cartilage at a specific height for precise cutting. U.S. Pat. No. 8,562,614 describes a disposable cartilage cutter featuring two plates with recesses that allow cartilage to form discs as a blade cuts the cartilage between the plates, leaving behind discs of cartilage that were located in the recess. This is a form of a thickness cutter, but the present invention uses a longitudinal blade on a vertically adjustable platform, and is adaptable to any shape and range of thickness (not just preformed discs). U.S. Pat. No. 6,491,511 describes molds for cutting of flat membranous tissue into specific a configuration that results in formation of heart valves to be used in cardiac surgery. Instead, the present invention focuses on ear/nose/eyelid, not heart valve shapes and configurations.

Other generally-related art include the following US patent documents:

U.S. Pat. No. 8,568,480—Joint arthroplasty devices and surgical tools.
U.S. Pat. No. 7,618,653—Biological artificial nerve guide and method of marking.
U.S. Pat. No. 7,156,814—Apparatus and method for harvesting and handling tissue samples for biopsy analysis.
U.S. Pat. No. 8,028,837—Break-open package with shaped die cut for storing and dispensing substrates.
U.S. Pat. No. 7,229,820—Apparatus and method for culturing and preserving tissue constructs.
U.S. Pat. No. 6,027,773—Specialty die cut confetti and method of manufacture.
U.S. Pat. No. 5,788,625—Method of making reconstructive SIS structure for cartilaginous elements in situ.
U.S. Pat. No. 5,653,749—Prefabricated, sterile, disposable kits for rapid assembly of a tissue heart valve.
U.S. Pat. No. 5,609,600—Tissue cutting die.
U.S. Pat. No. 5,425,741—Tissue cutting die.
U.S. Pat. No. 5,326,370—Prefabricated sterile and disposable kits for the rapid assembly of a tissue heart valve.
20120189669—Solid forms for tissue repair.
20100075896—Repair of larynx, trachea, and other fibrocartilaginous tissues.
20080039954—Expandable cartilage implant.
20070270948—Methods and composition for soft tissue feature reconstruction.

SUMMARY OF THE INVENTION

The present invention provides for an extremely easy-to-use, press-like device that allows for the production of precise ear, nose, and eyelid cartilage frameworks for efficient reconstruction of these structures, producing precise and symmetrical results, while removing variability, increasing reproducibility, and reducing costs and operative time. Anyone with a surgical training would be able to easily use this invention, which could provide every operating room with a device that can transform the medical response to devastating facial injuries. This device can be very relevant to medically underserved areas, allowing for quick and reliable reconstructions from any surgeon to any patient in need. The present device and process involves the generation of specific configurations of autologous cartilage or another dense synthetic implantable material such that, upon assembly, the final product can resemble the desired structure to be replaced.

This present invention preferably provides two distinct devices and the overall process by which one can build a three-dimensional replica of the human ear, nose, or eyelid tarsus from an initial substrate. This initial substrate can include materials such as autologous cartilage, as is currently derived from costochondral tissue, cadaveric cartilage, or commercially available dense implantable materials such as, but not limited to, acellular dermal matrix.

According to a first aspect of the present invention, apparatus for constructing a cartilage structure has a first plate, and a blade mounted over the first plate. The blade has (i) a predetermined shape, and (ii) a cutting edge protruding from the first plate and configured to cut a cartilage into the predetermined shape. A second plate has a guide imprint adjacent a surface thereof, the guide imprint having a shape complimentary to the predetermined shape of the blade. A press has (i) a first surface configured to mount the first plate, and (ii) a second surface configured to mount the second plate. Actuation structure is configured to press together the first and second surfaces to thereby cause the blade to cut the cartilage in the predetermined shape.

According to a second aspect of the present invention, a method of constructing a three-dimensional cartilage structure provides a press having a first surface and a second, opposed surface. A first plate is removably mounted on the first surface, the first plate having a cutting blade mounted thereover, the cutting blade having (i) a predetermined shape, and (ii) a cutting edge protruding from the first plate and configured to cut a cartilage into the predetermined shape. A second plate is removably mounted on the second surface, the second plate having a guide imprint adjacent a surface thereof, the guide imprint having a shape complimentary to the predetermined shape of the blade. The press first and second surfaces are pressed together to thereby cause the blade to cut the cartilage in the predetermined shape. The removable mounting and pressing steps are repeated to provide a second cartilage in a second predetermined shape. The cartilage and the second cartilage are then joined together into the three-dimensional cartilage structure. In an alternative, multiple blades and imprints can be provided on the plates to cut the multiple cartilages in a single operation.

Alternate embodiments of the first aspect of the present invention accomplish the same goal to cut a cartilage into the predetermined shape. These alternate embodiments do not utilize a press, but rather are one or more handheld cutting blades. Each blade preferably has (i) a predetermined shape substantially the same as those found on the cutting plate(s), and (ii) a handle protruding from the blade to provide the user with a means to safely transmit force through the blade onto the cartilage. Manual pressure applied through the handle against cartilage placed below the blade will thereby allow the blade to cut the cartilage in the predetermined shape. Such alternative embodiments will allow the user to cut cartilage and other similar implantable substrates, such as acellular dermal matrix that, for whatever reason, may not be utilized within the press architecture.

BRIEF DESCRIPTION OF THE DRAWINGS

Certain aspects in accordance with embodiments of the present invention are described below in connection with the accompanying drawing figures in which:

FIGS. 1A, 1B, 1C, and 1D are perspective, schematic drawings of ear reconstruction components;

FIG. 6A is a perspective, schematic drawing of a cutter press according to a preferred embodiment of the present invention, with the press open and no cassettes yet installed;

FIG. 6B is a perspective, schematic drawing of the cutter press of FIG. 6A, with the press open and example nose reconstruction cassettes installed;

FIGS. 7A, 7B, 7C, and 7D are perspective, schematic drawings of ear reconstruction handled cutters according to another preferred embodiment of the present invention;

FIGS. 7E, 7F, 7G, 7H, and 7I are perspective, schematic drawings of nose reconstruction handled cutters according to another preferred embodiment of the present invention;

FIGS. 8A, 8B, and 8C are schematic are schematic drawings showing the installation of an ear structure;

FIGS. 10A, 10B, and 10C are schematic drawings showing the installation of a eyelid structure.

DETAILED DESCRIPTION OF THE PRESENTLY PREFERRED EXEMPLARY EMBODIMENTS

Figure 2A:
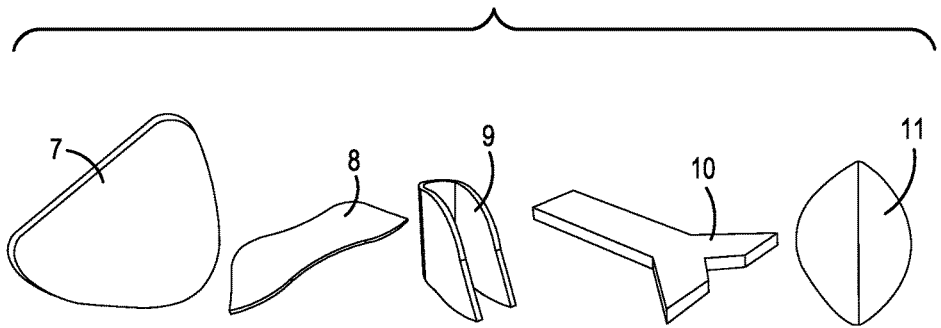
FIGS. 2A, 2B, 2C, and 2D are perspective, schematic drawings of nose reconstruction components.

Briefly, in the present invention, the surgeon preferably begins with a cartilage and/or other similar reconstructive material substrate, such as an acellular dermal matrix or a synthetic commercially-available cartilage, and processes that substrate into the desired shape and/or size. In overview, the substrate is preferably first cut by hand using a scalpel or other handheld cutting device into rough predetermined sizes in accordance with the desired component to be molded by this process, guided by recommendations for sizes dictated by the die corresponding to that component. Second, this roughly-cut substrate is sliced in the transverse plane by a first device, preferably a thickness cutter, which generates a piece of substrate at a predefined thickness. Third, this thinned substrate is placed into a press. Force applied by the operator pressing the die of that specific shape into the substrate, generating the desired shape in that substrate. Alternatively to the third step, the thinned substrate may be directly hand-cut by a specially shaped blade affixed to a handle. For ear reconstruction, the device will preferably create four distinct shapes, which, when assembled, will replicate the human ear or any subcomponent of the ear. For nose reconstruction, the device will preferably create four distinct shapes, which, when assembled, will replicate the human nose or any subcomponent of the nose. For eyelid reconstruction, the device will preferably create one distinct shape.

FIGS. 1A, 1B, 1C, and 1D illustrate the reconstruction of human ear cartilage from fabricated components made of human cartilage and/or animal cartilage and/or other useful material such as, but not limited to, acellular dermal matrix, or a combination of these. Member 1 is the base of the ear cartilage. Member 2 is the crux of the ear. Member 3 is the antihelix. Members 1 and 2 are preferably joined together at points 11, 12, 13, and 14 by fine resorbable or non-resorbable suture material; of course, fixatives and/or glues may be used. The thus-fused structure, Member 4, is then preferably joined with Member 3 at points 15, 16, 17, and 18 (FIG. 1B) by knots of fine suture material. This completed structure (a cartilage-based prosthetic, construct, structure), Member 5, is the completed model of the human ear. Member 6 is preferably a curved structure that serves to lift Member 5 away from the skull, thereby bringing the orientation of Member 5 closer to that of the true human ear. FIG. 1D depicts a completed ear structure with Member 6 providing structural (three-dimensional) protrusion of the ear from the (bone) surface on which the structure is implanted. Member 6 can be accordingly curved in a manner not limited to that which is depicted in FIG. 1D so as to achieve aesthetic results by the surgeon closest to that of a true human ear. Member 6 is preferably joined to Member 5 at Points 19 and 20 by knots of fine suture material. Of course, fixatives, epoxies, and/or glues may be used to join the various members.

Figure 2B:
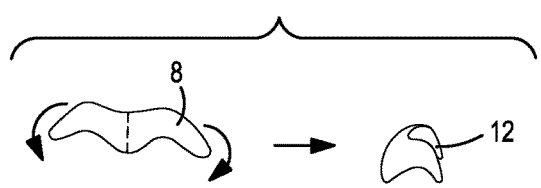
Figure 2C:
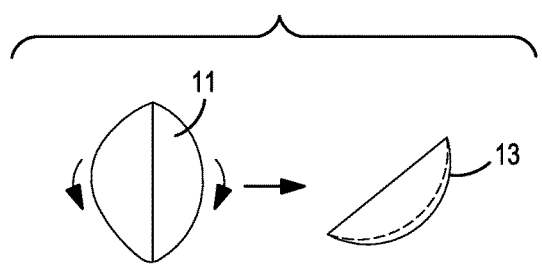
Figure 2D:
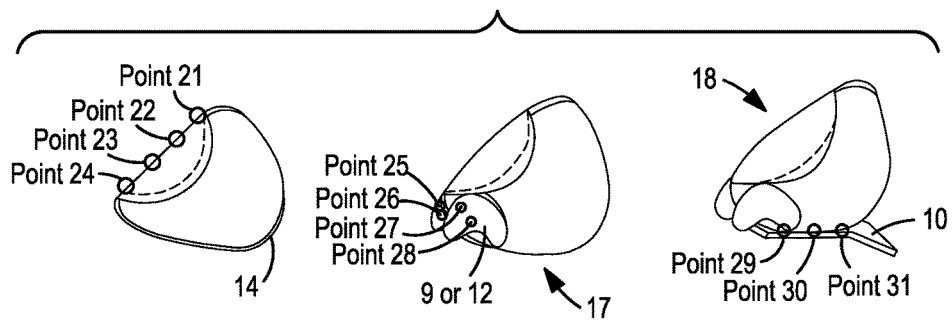

FIGS. 2A, 2B, 2C, 2D illustrate the reconstruction of human nose cartilage from fabricated components. Member 7 preferably comprises the septal cartilage. Members 8 and 9 preferably comprise the alar cartilages (two for a typical nose reconstruction), Member 10 preferably comprises the columellar strut cartilage, and Member 11 preferably comprises the lateral strut cartilage. As shown in FIG. 2B, Member 8 is preferably folded to form a C-shaped structure, Member 12. Likewise, as shown in FIG. 2C, Member 11 is folded along its midline to form a C-shaped structure, Member 13. As shown in FIG. 2D, Members 13 and 7 are joined together points 21, 22, 23, and 24 preferably using resorbable and/or non-resorbable sutures, forming Member 14. As shown in FIG. 2D, two copies of Members 9 or 12 are joined to Member 14 on either side of the septal cartilage at points 25, 26, 27, and 28 using resorbable and/or non-resorbable sutures, thus forming Member 17. As shown in FIG. 2D, Member 10 is joined to the underside of Member 17 at points 29, 30, and 31, thus forming Member 18. Attachment to the underlying fascia and overlying skin is preferably accomplished using resorbable and/or non-resorbable suture material in a manner determined by the surgeon to deliver the most optimal aesthetic draping of skin and soft tissue over the structure. The overall completed structure comprising Members 7, 8, 9, 10, and 11 is depicted as Member 18. Fusions of structures are preferably made using fine suture material, and the sites of recommended, but not limited, suture knots.

FIGS. 3A, 3B, 3C, 3D, 3E, 3F, 3G, 3H, 3I, and 3J show the preferred modular cutter cassettes that serve as the stamping dies to generate the aforementioned fabricated components. Each cassette preferably comprises a 75 mm×75 mm×4 mm square metal or rigid plastic plate 112. Each of cutter cassettes preferably has a thin metal protrusion of 1 centimeter height (although protrusions of 0.25, 0.5, 0.75, 1.25, and/or 1.5 cm height may be used) in a specific configuration as shown. Materials for this protrusion preferably include aluminum or steel blades fashioned in the precise configuration required to generate the shapes of the aforementioned fabricated components. The protrusions may be sharpened at the cutting edges. Of course, the sizes and relative proportions of the protrusions may vary depending upon the size/age of the patient. Preferably, the plate is mounted on a metal or plastic base.

Figure 3A:
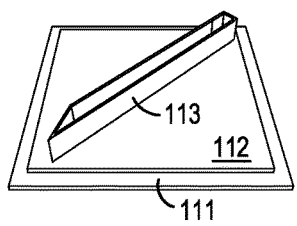
FIGS. 3A, 3B, 3C, and 3D are perspective, schematic drawings of ear reconstruction cutter cassette portions according to another preferred embodiment of the present invention.
Figure 3B:
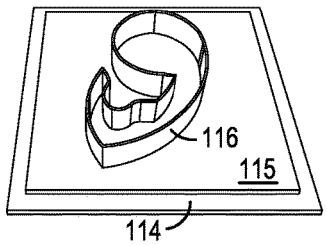
Figure 3C:
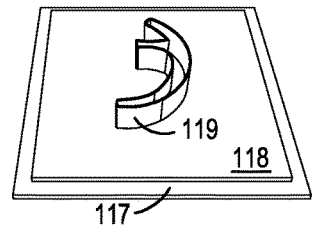
Figure 3D:
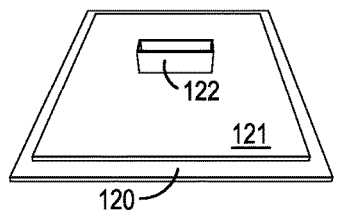
Figure 3E:
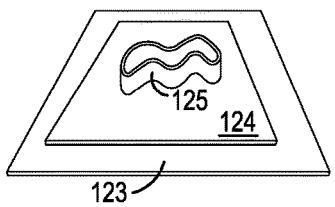
FIGS. 3E, 3F, 3G, 3H, and 3I are perspective, schematic drawings of nose reconstruction cutter cassette portions according to another preferred embodiment of the present invention.
Figure 3F:
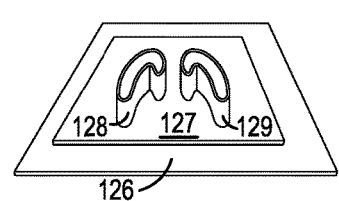
Figure 3G:
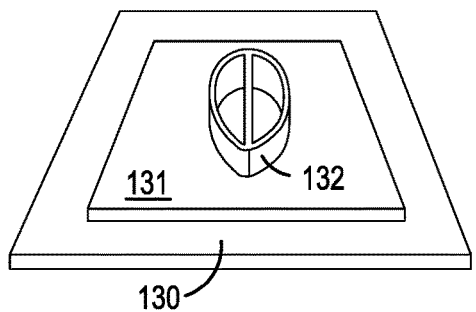
Figure 3H:
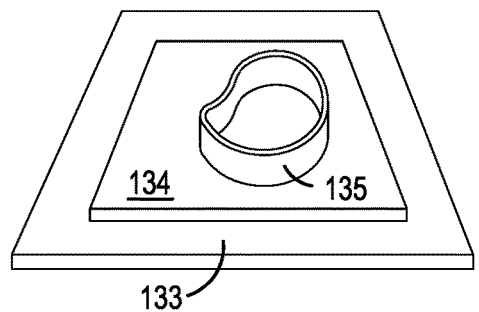
Figure 3I:
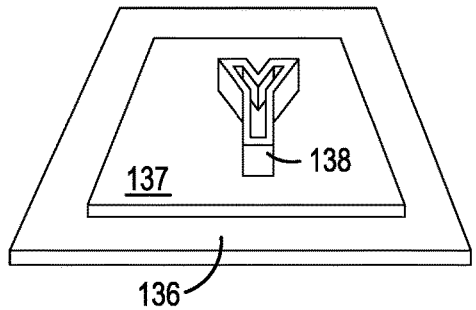
Figure 3J:
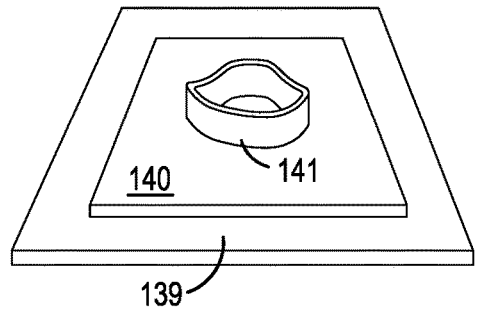
FIG. 3J is a perspective, schematic drawing of the eyelid tarsus reconstruction cutter cassette portion according to another preferred embodiment of the present invention.
Figure 4A:
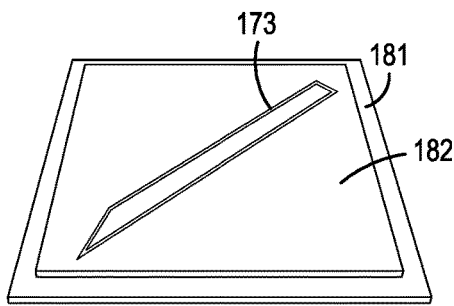
FIGS. 4A, 4B, 4C, and 4D are perspective, schematic drawings of ear reconstruction guide cassette portions according to another preferred embodiment of the present invention.
Figure 4B:
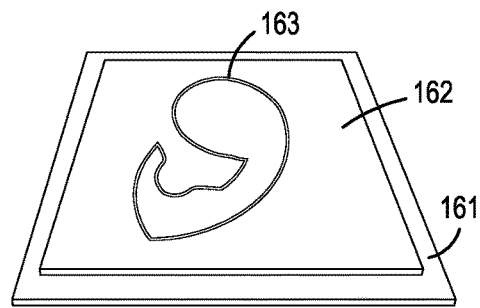
Figure 4C:
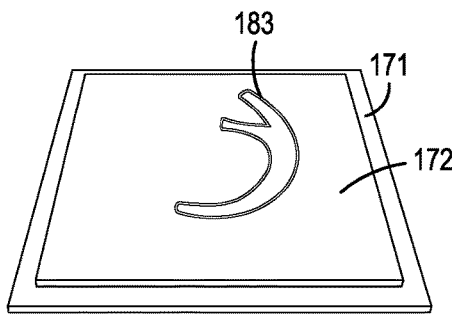
Figure 4D:
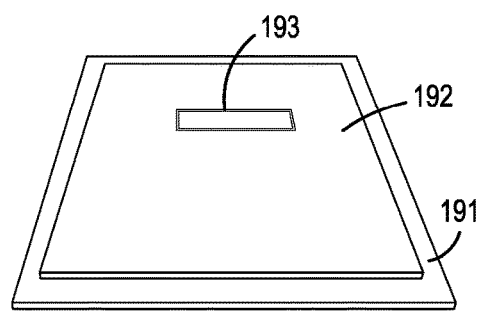
Figure 4E:
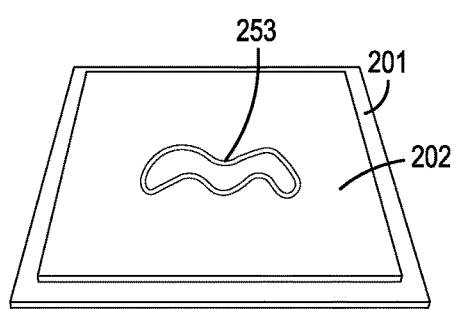
FIGS. 4E, 4F, 4G, 4H, and 4I are perspective, schematic drawings of nose reconstruction guide cassette portions according to another preferred embodiment of the present invention.
Figure 4F:
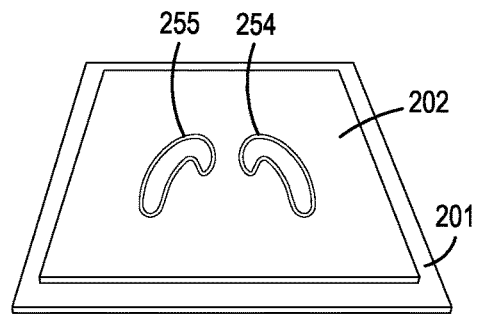
Figure 4G:
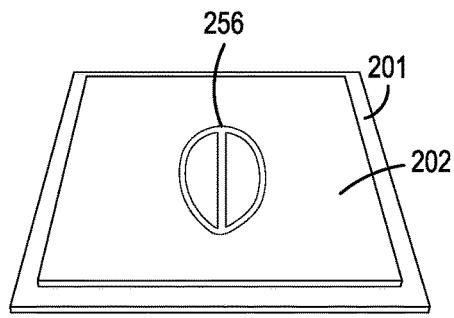
Figure 4H:
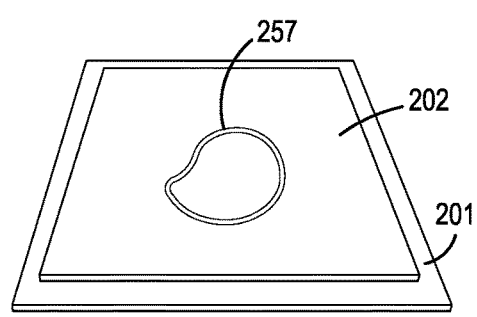
Figure 4I:
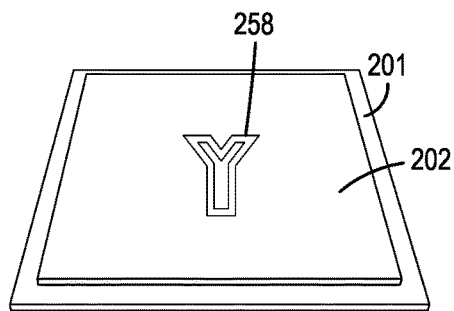
Figure 4J:
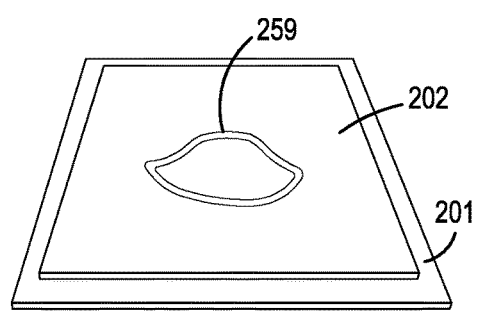
FIG. 4J is a perspective, schematic drawing of the eyelid tarsus reconstruction guide cassette portion according to another preferred embodiment of the present invention.

For example, FIG. 3A may comprise a base 111, a plate 113, and a cutter blade 113 (which cuts the member 3). In FIG. 3B, the plate 115 is mounted on base 114 and supports blade 116 (which cuts member 1). FIG. 3C comprises the base 117, the plate 118, and blade 119 (which cuts the member 2). FIG. 3D has a base 120, a plater 121, and a cutter 122 (which cuts the member 6). FIG. 3E comprises the base 123, the plate 124, and the cutter 125 (which cuts the member 8). FIG. 3F shows the base 126, the plate 127, and cutters 128 and 129 (which cut member 9). FIG. 3G depicts the base 130, the plate 131, and the blade 132 (which cuts member 11). FIG. 3H shows the plater 133, plate 134, and cutter 135 (which cuts member 7). FIG. 3I depicts base 136, plate 137, and blade 138 (which cuts member 10). FIG. 3J shows the base 139, the plate 140, and the cutter 141 (which cuts member 1011).

In greater detail, FIG. 3A, the rectilinear (or other-shape) plate 111 supports a rectilinear (or other-shape) substrate 112, each made of rigid plastic or metal such as steel and/or aluminum. Plate 111 is of dimensions 85 mm×85 mm×2 mm and substrate 112 is of dimensions 75 mm×75 mm×2 mm. The ear antihelix cutting blade 113 is supported on the substrate 112 by a firm adhesive. In FIG. 3B, the rectilinear (or other-shape) plate 114 supports a rectilinear (or other-shape) substrate 115, which in turn supports the ear base cutting blade 116. In FIG. 3C, the rectilinear (or other-shape) plate 117 supports a rectilinear (or other-shape) substrate 118, which in turn supports the ear crus cutting blade 119. In FIG. 3D, the rectilinear (or other-shape) plate 120 supports a rectilinear (or other-shape) substrate 121, which in turn supports the ear posterior wedge cutting blade 122.

In FIG. 3E, the rectilinear (or other-shape) plate 123 supports a rectilinear (or other-shape) substrate 124, each made of rigid plastic. Plate 123 is of dimensions 85 mm×85 mm×2 mm and substrate 124 is of dimensions 75 mm×75 mm×2 mm. The nose alar cartilage side cutting blade 125 is supported on the substrate 124 by a firm adhesive. In FIG. 3F, the rectilinear (or other-shape) plate 126 supports a rectilinear (or other-shape) substrate 127, which in turn supports the nose alar cartilage vertical cutting blade 128. In FIG. 3G, the rectilinear (or other-shape) plate 130 supports a rectilinear (or other-shape) substrate 131, which in turn supports the nose lateral cartilage blade 132. In FIG. 3H, the rectilinear (or other-shape) plate 133 supports a rectilinear (or other-shape) substrate 134, which in turn supports the nose septum cutting blade 135. In FIG. 3I, the rectilinear (or other-shape) plate 136 supports a rectilinear (or other-shape) substrate 137, which in turn supports the nose columellar strut cutting blade 138.

In FIG. 3J, the rectilinear (or other-shape) plate 139 supports a rectilinear (or other-shape) substrate 140, each made of rigid plastic. Plate 139 is of dimensions 85 mm×85 mm×2 mm and substrate 140 is of dimensions 75 mm×75 mm×2 mm. The eyelid tarsus blade 141 is supported on the substrate 140 by a firm adhesive.

FIGS. 4A, 4B, 4C, 4D, 4E, 4F, 4G, 4H, 4I, and 4J show the preferred modular guide cassettes that preferably have imprinted outlines of the corresponding shapes on the surfaces of the cassettes, either in ink or engravings. If engraving, the trough may be 0.1 to 0.5 cm deep. The guide cassettes may also contain small (1 mm) rigid plastic or metal protrusions or pins around the imprinted outline to secure the substrate material in place during the cutting action. When aligned and opposed, the metal protrusion on the cutter cassette precisely overlays the outline imprinted on the guide cassette. Each guide cassette preferably respectively includes a rectilinear (or other-shape) base. For example, guide cassettes preferably have imprinted outlines of the corresponding shapes 163, 173, 183, 193, 253, 254, 255, 256, 257, 258, and 259 on the surfaces of the cassettes, either in ink or engravings. If engraving, the trough may be 0.1 to 0.5 cm deep. When aligned and opposed, the metal protrusion on the cutter cassette precisely overlays the outline imprinted on the guide cassette. Each guide cassette preferably respectively includes a rectilinear (or other-shape) base 161, 171, 181, 191, and 201, supporting a respective substrate 162, 172, 182, 192, and 202.

Figure 5A:
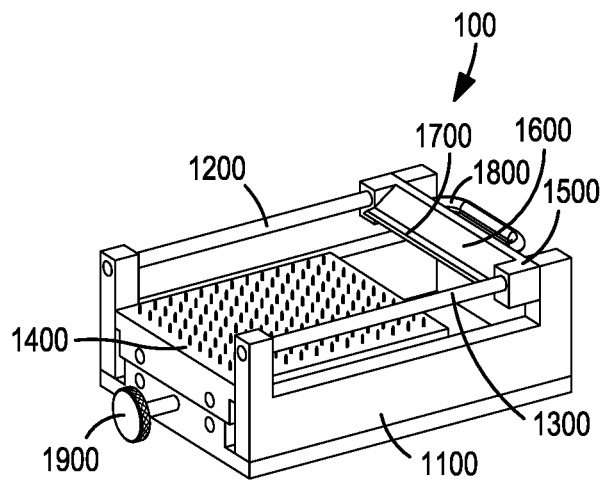
FIG. 5A is a front-perspective, schematic drawing of a thickness cutter according to another preferred embodiment of the present invention.
Figure 5B:
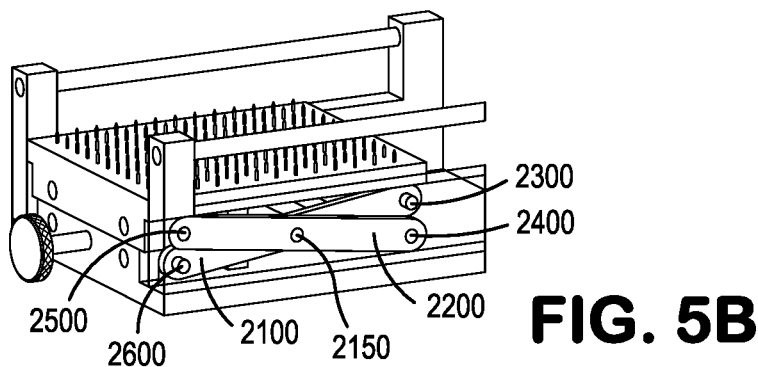
FIG. 5B is another partially hidden, front-perspective, schematic drawing of a thickness cutter according to another preferred embodiment of the present invention.
Figure 5C:
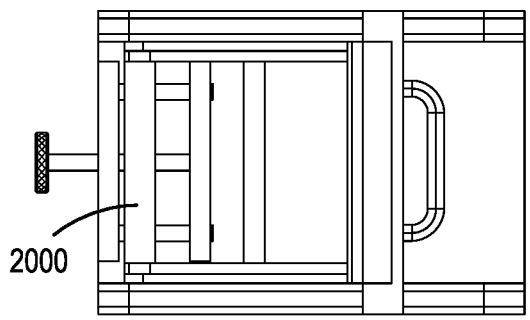
FIG. 5C is a bottom-perspective, schematic drawing of a thickness cutter according to another preferred embodiment of the present invention.

FIGS. 5A, 5B, and 5C illustrate the thickness cutter Member 100. FIG. 5A illustrates Member 100 from a frontal oblique view. FIG. 5B illustrates Member 100 from a frontal oblique view with one of the base structure walls (Member 1100) hidden. FIG. 5C illustrates Member 100 from a bottom view to detail the platform mechanism. Member 100 preferably comprises a base structure (Member 1100) with two longitudinal slider rods (Members 1200 and 1300) and vertically moving platform (Member 1400). The longitudinal slider rods serve as a guidance track for the sliding blade, which preferably comprises a frame (Member 1500) a transverse blade support structure (Member 1600) which securely holds a steel blade (Member 1700) of sufficient strength and thickness to reliably cut substrate material with precision to within +/−0.5 millimeter, and can be replaced if necessary. The frame (Member 1500) is attached to a handle (Member 1800) which the operator uses to exert force on frame, resulting in the blade structure sliding along the rods (Members 1200 and 1300) longitudinally across the platform. At the opposing end of the base structure is an adjustable platform (Member 1400). This platform can be adjusted to a specific height with respect to the surrounding base plate, for example, at predetermined heights from 0-30 millimeter difference in height from the surrounding base structure.

Preferably, an external dial (Member 1900) controls a mechanical converter as diagrammed in FIG. 5C that results in vertical translation of the platform to a desired and specific value corresponding to platform deviation from 0-30 mm through rotation of that dial. Rotation of the dial (Member 1900) by the operator results in translation of this rotation force to a horizontally-oriented beam (Member 2000). Movement of this horizontal beam results in a scissoring motion of two sliding plates (Members 2100 and 2200) joined by a hinge at their midpoint 2150. Members 2100 and 2200 are joined to the base structure by several pivot points allowing for their vertical movement. Pivots 2300 and 2400 are fixed in the horizontal dimension while Pivots 2500 and 2600 are horizontally translatable. The superior aspects of these sliding plates are preferably fused to the platform (Member 1400). Thus, turning of Member 1900 by the operator can result in horizontal movement of Member 2000 and Pivots 2500 and 2600, producing a scissoring action of Members 2100 and 2200, in turn resulting in an even vertical movement of the platform. The dial (Member 1900) also contains markings, which indicate the relative height of the platform with respect to the table. The substrate is placed onto the platform and may be secured by pins that pierce the substrate tissue, or vertical clamps to mechanically secure the substrate material to the platform.

The thickness cutter thus preferably comprises a long, horizontally oriented blade affixed to a sliding frame with an attached handle. Applying force to the handle, the blade-post structure can slide laterally along slider rods that guide its linear path. The substrate is secured by clips or pins on a platform that is located at the end of the linear path of the blade. The platform can be raised or lowered by the operator by turning a dial with markings indicating the resulting height of the platform relative to a baseline value. Lateral movement of the blade over this platform results in the cutting of the substrate into a thinner substrate of user-defined thickness.

FIGS. 6A and 6B illustrate the press, which preferably comprises a base plate (Member 3000; 14 cm×14 cm, aluminum or another rigid material). The base plate 3000 preferably contains an insert (Member 3100) of appropriate dimension and size (for example 9.5 cm×11.8 cm×1 cm with an inset of 7.6 cm×10.8 cm×2 cm made of aluminum or another rigid material) to allow entrance and security of a guide cassette with dimensions 7.5 cm×7.5 cm. The base plate also preferably contains two vertical posts (Members 3200, 3300), which support a horizontal rod (Member 3400). This horizontal rod serves as a hinge for the rotation of the roof plate (Member 3500). The roof plate preferably contains an inset (Member 3600) of appropriate dimension and size (for example 14 cm×9.5 cm with an inset of 8 cm×8.6 cm×2 cm and aluminum or another rigid material) to allow entrance of a cutter cassette and a reversible locking mechanism, which secures the cutter cassette in place in the inset (Member 3600).

The roof plate is preferably attached to a handle (Member 3700), which the operator uses to apply force to lift and lower the roof plate with respect to the base plate, with the hinge guiding the relative rotation of the plates against each other. FIG. 6B illustrates the introduction of guide cassette 3800 and cutter cassette 3900 into their respective insets on the base and roof plates and the placement of a substrate on the guide cassette.

The press thus comprises a base platform, a hinge, and a roof plate with an affixed handle. The base platform comprises a flat metal surface supporting a second smaller plate, which serves as a receptacle for the guide cassette. The guide cassette is a flat metal plate specific for each desired shape and contains a visual outline of shape to be cut and the location on the plate where, if a substrate was present, a cut will be made by the overlying cutter cassette. The guide cassette inserts into the receptacle of the base plate by sliding along grooves that fit the specific contour of the guide cassette.

The roof plate similarly contains a receptacle for a cutter cassette. The cutter cassette is specific for each desired shape and comprises a flat metal plate with an outline of the desired shape generated by a thin metal blade. The cutter cassette slides into the receptacle on the roof plate along grooves that fit the specific contour of the cutter cassette. Once the operator has inserted a guide cassette and its corresponding cutter cassette into the base and roof plates, respectively, the operator then places the thickness-specified substrate onto the guide cassette, covering the entirety of the shape outlined on the guide cassette. The operator then applies downward force on the handle on the roof plate, pressing the cutter cassette against the substrate and guide cassette, with elastic resistance generated by springs associated with the hinge mechanism. Once sufficient force has been applied to bring the cutter and guide cassettes together, the operator releases applied force, and the substrate has been cut into the specified shape.

FIGS. 7A, 7B, 7C, 7D, 7E, 7F, 7G, 7H, 7I, and 7J illustrate the handled cutters, which serve as an alternative option for the user to mold the cartilage to those shapes generated by the cutter cassettes without using the press architecture. The handled cutter preferably comprises the same blade configuration as in its corresponding cutter cassette, but is affixed, in this case, to a small handle of sufficient size to be held comfortably by a single hand. In this manner, the operator places a predetermined thickness-specified piece of cartilage onto the guide cassette or any sterile, flat surface. The operator holds these cutting devices at its handle and controls the positioning and downward force applied through the handle into the blade. This downward force, combined with the sharpness of the blade, will be sufficient to cut the provided cartilage, acellular dermal matrix, or other implantable substrate into the preconfigured shape.

In FIG. 7A, Handle 150 is affixed to Blade 151, which, when pressed against a substrate material such as cartilage, acellular dermal matrix, or implantable synthetic materials, will cut the outline of the ear antihelix. In FIG. 7B, Handle 152 is affixed to Blade 152, which, when pressed against a substrate, cuts the outline of the ear base. In FIG. 7C, Handle 154 is affixed to Blade 155, which, when pressed against a substrate, cuts the outline of the ear crus. In FIG. 7D, Handle 156 is affixed to Blade 157, which, when pressed against a substrate, cuts the outline of the ear posterior wedge.

Figure 7I:
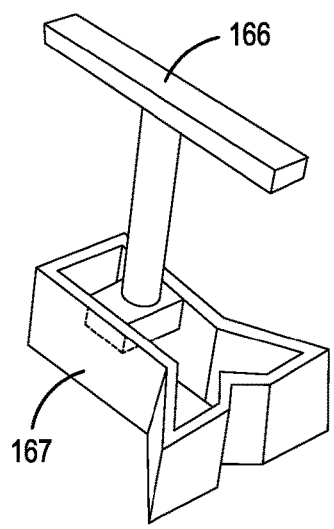

In FIG. 7E, Handle 158 is affixed to Blade 159, which, when pressed against a substrate material such as cartilage, acellular dermal matrix, or implantable synthetic materials, will cut the outline of the nose alar cartilage from the horizontal perspective. In FIG. 7F, Handle 160 is affixed to Blade 161, which, when pressed against a substrate, cuts the outline of the nose alar cartilage from the vertical perspective. In FIG. 7G, Handle 162 is affixed to Blade 163, which, when pressed against a substrate, cuts the outline of the nose lateral cartilage. In FIG. 7H, Handle 164 is affixed to Blade 165, which, when pressed against a substrate, cuts the outline of the nose septal cartilage. In FIG. 7I, Handle 166 is affixed to Blade 167, which, when pressed against a substrate, cuts the outline of the nose columellar strut cartilage.

Figure 7J:
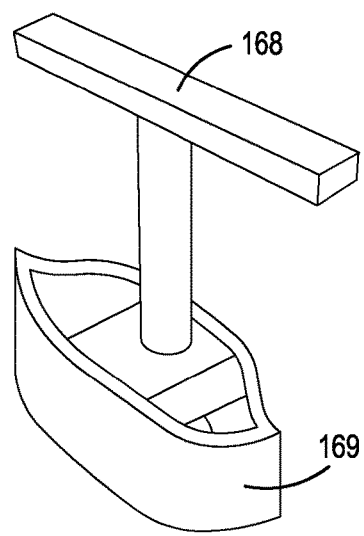
FIG. 7J is a perspective, schematic drawing of eyelid tarsus reconstruction handled cutter according to another preferred embodiment of the present invention.

In FIG. 7J, Handle 168 is affixed to Blade 169, which, when pressed against a substrate material such as cartilage, acellular dermal matrix, or implantable synthetic materials, will cut the outline of the eyelid tarsus cartilage from the horizontal perspective.

With reference to FIGS. 8A, 8B, and 8C, to reconstruct an ear of a patient 8100, the operator will typically generate four shapes using the thickness cutter and press: the base, the crus, the antihelix, and the posterior wedge. The crus is affixed to the base and sutured to secure those components. The antihelix is wrapped around the outer curve of the base piece and sutured to secure those components. The completed ear replica 8300 is then inserted into the skin 8200 using established surgical techniques. The posterior wedge component is utilized by the surgeon to provide protrusion of the completed ear replica from the head to a degree that will match ear protrusion on the contralateral side. The structure is then sewn to the skin with appropriate knots and sutures (as noted above), an opening 8400 is made (if necessary) for the ear canal, and appropriate bandages are applied for the healing process.

Figures 9A, 9B, 9C:
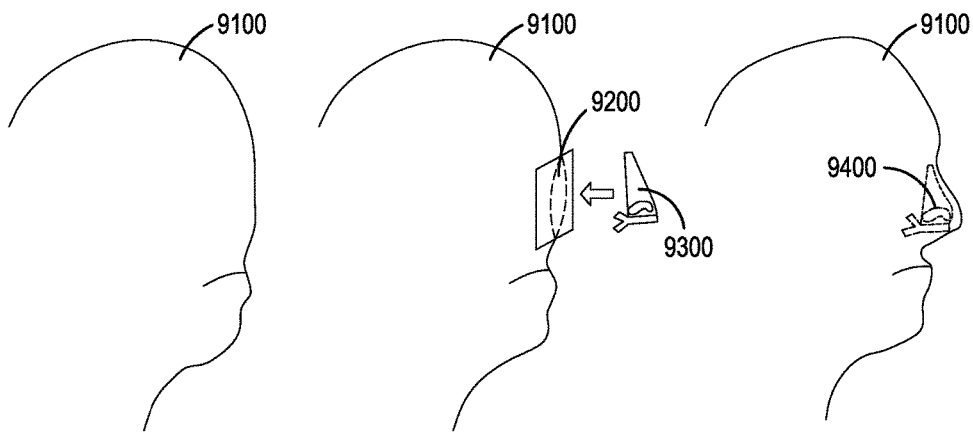
FIGS. 9A, 9B, and 9C are schematic drawings showing the installation of a nose structure.

Similarly, with reference to FIGS. 9A, 9B, and 9C, to reconstruct a nose of a patient 9100, the operator will generate four distinct shapes using the thickness cutter and press: the septal cartilage, the lateral cartilage, the alar cartilages, and columellar strut. The lateral cartilage is folded along its midsection to form a cupped shape. The lateral cartilage is secured by sutures to the septal cartilage along the midline of its structure. The alar cartilage can be formed in one of two ways depending on the dimensions of the substrate material available for molding. If the substrate material is of sufficient thickness, the alar cartilage can be formed using the vertical alar cassette, the product of which will not require bending or forceful reshaping. However, if the substrate material is thin, the alar cartilage can be alternatively formed using the longitudinal alar cassette, the product of which must be folded along its midsection to form a cupped shape. The alar cartilage is secured by sutures to both the inferior border of the lateral cartilage as well as the septal cartilage. The columellar strut is secured to the base of the septal cartilage by sutures. Using a classic staircase open rhinoplasty incision through the columella, the tissue is elevated and the nose is degloved at 9200 to expose the cartilaginous structures that require repair. Once those are fabricated using this device, the cartilage 9300 is anchored to the remaining cartilaginous structures of the nose or to the maxillary bone, via sutures and/or surgical glues, etc. The cartilage pieces are preferably assembled using wire sutures, resorbable and/or non-resorbable suture and the skin is draped over the newly reconstructed framework 9400 and the incision is closed with resorbable suture.

Similarly, with reference to FIGS. 10A, 10B, and 10C, to reconstruct an eyelid 1009 of patient 1010, the operator will generate a thin, ellipse-shaped cartilaginous structure (eyelid tarsus) 1011 that can be used for reconstruction of the tarsal plate, the semi-rigid structure of the upper eyelid to which muscles and tendons attach to allow the opening of the eye. The tarsal cartilage generated will be inset in the upper eyelid using a small trans-conjunctival incision or transcutaneous incision. This cartilage may also be generated at higher thickness to produce a weigh-effect to correct the inability to lower the upper eyelid (such as in Bell palsy), which can lead to corneal damage and blindness.

Thus the present invention provides advantageous structure and/or function including at least the following advantages: (i) An apparatus for efficiently and accurately cutting shapes of precise configuration from a given implantable substrate, with the apparatus comprising a movable cutting surface that cuts the substrate into dimension-specific configurations; (ii) An apparatus for slicing an implantable substrate into a substrate of defined thickness, with the apparatus comprising a vertically adjustable stage with various possible mechanisms (adhesive/low-friction materials, pins, or vertical clamps) to secure the substrate onto the stage, a replaceable horizontally oriented blade of sufficient length to cover the entirety of the stage, and a handled structure supporting the blade, which, when acted on by the operator, follows a defined path to laterally displace the blade over the stage to cut the substrate in the longitudinal plane; and (iii) A set of dies and handled cutting blades, comprising of vertically oriented blades perpendicular to a supporting surface, configured in specific shapes to form the outline of the following structures:

a. The flat, inner curved base of the cartilaginous component of the ear;
b. The forked crus of the cartilaginous component of the ear;
c. The outer antihelix of the cartilaginous component of the ear;
d. The posterior cartilaginous component to lift the ear away from the skull;
d. The lateral cartilaginous components of the nose;
e. The median septal cartilage of the nose;
f. The alar cartilaginous components of the nose;
g. The midline strut cartilage of the nose; and
h. The tarsus cartilage of the eyelid.

Further advantageous features include: (iv) A set of variably sized dies with the configurations defined above, but of similar proportion to those previously defined configurations, allowing for cutting of substrates to form shapes of different sizes but similar shape; (v) A modular system by which dies can be interchangeably inserted and removed into the apparatus defined above such that this single apparatus can support each of the different dies, allowing this single apparatus to cut different configurations from a provided substrate; and (vi) The overall process by which the implantable substrate is processed by a combination of manual and apparatus-assisted processes to generate shape-specific components, and the subsequent assembly of those components into a 3-dimensional model of the cartilaginous frameworks of the ear, nose, or eyelid so as to implant the assembled structure into soft tissue structures in the body.

Although the foregoing invention has been described in terms of certain preferred embodiments, other embodiments will become apparent to those of ordinary skill in the art in view of the disclosure herein. Accordingly, the present invention is not intended to be limited by the recitation of preferred embodiments, but is intended to be defined solely by reference to the appended claims.

All US patent documents listed herein are specifically incorporated by reference into the Detailed Description of the Presently Preferred Exemplary Embodiments.

What is claimed is:

1. A method of constructing a three-dimensional facial cartilage structure, comprising:
   providing a press having a first surface and a second, opposed surface;
   removably mounting a first plate on the first surface, the first plate having a cutting blade mounted thereover, the cutting blade having (i) a predetermined shape, and (ii) a cutting edge protruding from said first plate and configured to cut a cartilage into the predetermined shape;
   removably mounting a second plate on the second surface, the second plate having a guide imprint adjacent a surface thereof, the guide imprint having a shape complimentary to the predetermined shape of the blade;
   pressing together the press first and second surfaces to thereby cause the blade to cut a first cartilage structure in the predetermined shape;
   repeating the removably mounting and pressing steps to provide a second cartilage structure in a second predetermined shape; and
   joining together the first cartilage structure and the second cartilage structure into the three-dimensional facial cartilage structure.

2. The method according to claim 1, wherein the blade comprises a shape corresponding to at least one of ear base, ear crus, and ear antihelix.

3. The method according to claim 1, wherein the blade comprises a shape corresponding to at least one of nose alar, nose lateral, nose septal, and nose strut.

4. The method according to claim 1, wherein the blade comprises a shape corresponding to eyelid tarsus.

5. The method according to claim 1, further comprising the step of providing a thickness-cutter blade which to cuts at least one of the first and second cartilage structures in a thickness direction.

6. The method according to claim 5, wherein the thickness-cutter blade is coupled to a thickness-cutter device having structure which translates the thickness-cutter blade in a horizontal direction.

7. The method according to claim 1, further comprising the step of installing the three-dimensional cartilage structure in a patient.

8. A method of constructing a three-dimensional facial cartilage structure, comprising:

provising a press having a first surface and a second, opposed surface;

removably mounting a first plate on the first surface, the first plate having first and second cutting blades mounted thereover, the first cutting blade having (i) a first predetermined shape, and (ii) a first cutting edge protruding from said first plate and configured to cut a cartilage into the first predetermined shape, the second cutting blade having (i) a second predetermined shape, and (ii) a second cutting edge protruding from said first plate and configured to cut the cartilage into the second predetermined shape;

removably mounting a second plate on the second surface, the second plate having first and second guide imprints adjacent a surface thereof, the first guide imprint having a shape complimentary to the first predetermined shape of the first cutting edge, the second guide imprint having a shape complimentary to the second predetermined shape of the second cutting edge;

pressing together the press first and second surfaces to thereby cause the blades to cut the cartilage structure in the first and second predetermined shapes; and joining together the cartilage first and second predetermined shapes to form the three-dimensional facial cartilage structure.

9. The method according to claim 8, further comprising the step of cutting a thickness of the cartilage.

10. The method according to claim 9, wherein the step of cutting a thickness of the cartilage is performed prior to the pressing step.

11. A method of constructing a three-dimensional facial cartilage structure, comprising:

providing a first handled cutter having (i) a first blade shaped to a first predetermined cartilage structure configuration and (ii) a first handle affixed to said first blade;

manually pressing the first handled cutter against a cartilage substrate, secured on a flat surface, to thereby cause the first blade to cut the cartilage substrate in the first predetermined configuration;

providing a second handled cutter having (i) a second blade shaped to a second predetermined cartilage structure configuration and (ii) a second handle affixed to said second blade;

manually pressing the second handled cutter against at least one of (i) the cartilage substrate and (ii) another cartilage substrate, which at least one substrate is secured on at least one flat surface, to thereby cause the second blade to cut the at least one cartilage substrate in the second predetermined configuration; and joining together the cartilage and the second cartilage into the three-dimensional facial cartilage structure.

12. The method according to claim 11, wherein the first blade comprises a shape corresponding to at least one of ear base, ear crus, and ear antihelix.

13. The method according to claim 11, wherein the first blade comprises a shape corresponding to at least one of nose alar, nose lateral, nose septal, and nose strut.

14. The method according to claim 11, wherein the first blade comprises a shape corresponding to eyelid tarsus.

* * * * *